(12) United States Patent
Chang et al.

(10) Patent No.: US 7,186,519 B2
(45) Date of Patent: *Mar. 6, 2007

(54) METHOD FOR DETECTING INTRACELLULAR CHOLESTEROL

(75) Inventors: Ta-Yuan Chang, Hanover, NH (US); Shigeki Sugii, West Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 173 days.

This patent is subject to a terminal disclaimer.

(21) Appl. No.: 10/293,788

(22) Filed: Nov. 13, 2002

(65) Prior Publication Data

US 2004/0091944 A1 May 13, 2004

(51) Int. Cl.
*C12Q 1/00* (2006.01)
*C12Q 1/60* (2006.01)

(52) U.S. Cl. .......................................... 435/11; 435/4

(58) Field of Classification Search .................. 435/4, 435/6, 11, 29
See application file for complete search history.

(56) References Cited

U.S. PATENT DOCUMENTS

| 6,465,258 B1 | 10/2002 | Shan et al. | 436/501 |
| 2002/0162124 A1 | 10/2002 | Farber et al. | 800/3 |
| 2004/0115613 A1* | 6/2004 | Chang | 435/4 |

FOREIGN PATENT DOCUMENTS

WO    WO 02/068681 A1 *   9/2002

OTHER PUBLICATIONS

Byers et al., "Niemann-Pick Type II fibroblasts exhibit impaired cholesterol esterification in response to *Sphingomyelin hydrolysis*", Biochimica et Biophysica Acta 1992 1138:20-26.
Cadigan et al., "Isolation and Characterization of Chinese Hamster Ovary Cell Mutants Defective in Intracellular Low Density Lipoprotein-Cholesterol Trafficking", J. Cell. Biol. 110:295-308.
Chang et al., "Regulation of Cytosolic Acetoacetyl Coenzyme A Thiolase, 3-Hydroxy-3-methylglutaryl Coenzyme A Synthase, 3-Hydroxy-3-methylglutaryl Coenzyme A Reductase, and Mevalonate Kinase by Low Density Lipoprotein and by 25-Hydroxycholesterol in Chinese Hamster Ovary Cells", J. Biol. Chem. 1980 255(16): 7787-7795.
Cruz et al., "Fate of Endogenously Synthesized Cholesterol in Niemann-Pick Type C1 Cells", J. Biol. Chem. 2000 275 (52):41309-41316.
Cruz et al., "Role of Niemann-Pick Type C1 Protein in Intracellular Trafficking of Low Density Lipoprotein-derived Cholesterol", J. Biol. Chem. 2000 275 (6) :4013-4021.
Dahl et al., "Isolation and Characterization of Chinese Hamster Ovary Cells Defective in the Intracellular Metabolism of Low Density Lipoprotein-derived Cholesterol", J. Biol. Chem. 1992 267 (7) :4889-4896.
Gu et al., "Substantial narrowing of the Niemann-Pick C candidate interval by yeast artificial chromosome complementation", Proc. Natl. Acad. Sci. USA 1997 94:7378-7383.
Hagiwara et al., "Cross-Linking of Plasmalemmal Cholesterol in Lymphocytes Induces Capping, Membrane Shedding, and Endocytosis through Coated Pits", Biochem. Biophys. Res. Commun. 1999 260:516-521.
Hua et al., "Sterol Resistance in CHO Cells Traced to Point Mutation in SREBP Cleavage-Activating Protein", Cell 1996 87:415-426.
Iwamoto et al., "A biotinylated perfringolysin O derivative:A new probe for detection of cell surface cholesterol", Biochimica et Biophysica Acta 1997 1327:222-230.
Lange et al., "Cholesterol Movement in Niemann-Pick Type C Cells and in Cells Treated with Amphiphiles", J. Biol. Chem. 2000 275 (23) :17468-17575.
Liscum et al., "The Intracellular Transport of Low Density Lipoprotein-derived Cholesterol Is Defective in Niemann-Pick Type Fibroblasts", J. Cell. Biol. 108:1625-1636.
Möbius et al., "Immunoelectron Microscopic Localization of Cholesterol Using Biotinylated and Non-cytolytic Perfringolysin O", J. Histochem. Cytochem. 2002 50:43-55.
Nakamura et al., "Interaction of Ø-Toxin (Perfringolysin O), a Cholesterol-Binding Cytolysin, with Liposomal Membranes:Change in the Aromatic Side Chains upon Binding and Insertion", Biochemistry 1995 34:6513-6520.
Ohno-Iwashita et al., "Effect of lipidic factors on membrane cholesterol topology-mode of binding of Ø-toxin to cholesterol in liposomes", Biochimica et Biophysica Acta 1992 1109:81-90.
Ohno-Iwashita et al., "A Cytolysin, Ø-Toxin, Preferentially Binds to Membrane Cholesterol Surrounded by Phospholipids with 18-Carbon Hydrocarbon Chains in Cholesterol-Rich Region", J. Biochem. 1991 110:369-375.
Ohno-Iwashita et al., "A modified Ø-toxin produced by limited proteolysis and methylation:a probe for the functional study of membrane cholesterol" Biochimica et Biophysica Acta, 1990 1023:441-448.
Ohno-Iwashita et al., "Cold-Labile Hemolysin Produced by Limited Proteolysis of Ø-Toxin from *Clostridium perfringens*", Biochemistry 1986 25:6048-6053.
Patterson et al., "Niemann-Pick Disease Type C:A Lipid Trafficking Disorder", Lysosomal Disorders, Chapter 145 pp. 3611-3632.
Pentchev et al., "A defect in cholesterol esterification in Niemann-Pick disease (type C) patients", Proc. Natl. Acad. Sci. USA 1985 82:8247-8251.
Rossjohn et al., "Structure of a Cholesterol-Binding Thiol-Activated Cytolysin and a Model of Its Membrane Form", Cell 1997 89:685-692.
Waheed et al., Selective binding of perfringolysin O derivative to cholesterol-rich membrane microdomains (rafts), PNAS 2001 98 (9) :4926-4931.

* cited by examiner

*Primary Examiner*—Ruth A Davis
(74) *Attorney, Agent, or Firm*—Licata & Tyrrell P.C.

(57) ABSTRACT

The present invention relates to a method of detecting intracellular cholesterol. The method provides contacting a permeabilized cell with labeled Cθ complex. Methods of using this detection method to identify agents which modulate cholesterol accumulation in a cell are also provided.

4 Claims, No Drawings

METHOD FOR DETECTING INTRACELLULAR CHOLESTEROL

INTRODUCTION

This invention was made in the course of research sponsored by the National Institutes of Health (NIH Grant No. HL36709). The U.S. government may have certain rights in this invention.

BACKGROUND OF THE INVENTION

Microdomains, called lipid rafts, exist in all mammalian cell membranes. They are rich in cholesterol and sphingolipids, and play important roles in various cellular processes including signal transduction, cell surface polarity, and endocytosis (Simons and Ikonen (2000) *Science* 290:1721–6). Cholesterol also modulates intracellular transport of proteins from early endosomes to the plasma membranes, or from endosomes to the Golgi (Mayor, et al. (1998) *EMBO J.* 17:4626–38; Grimmer, et al. (2000) *Mol. Biol. Cell* 11:4205–16; Miwako, et al. (2001) *J. Cell Sci.* 114:1765–76) and the trafficking pathway of other lipids such as sphingolipids (Puri, et al. (1999) *Nat. Cell Biol.* 1:386–8; Puri, et al. (2001) *J. Cell Biol.* 154:535–47). One of the key molecules involved in the correct distribution of intracellular cholesterol is Niemann-Pick Type C1 (NPC1) protein; mutation in NPC1 causes NPC syndrome, a fatal pediatric neurodegenerative disease (Patterson, et al. (2001) In: The Metabolic and Molecular Bases of Inherited Disease, Scriver, et al. (ed) McGraw-Hill, New York p. 3611–3633). Chinese hamster ovary (CHO) mutants that are defective in the NPC1 protein have been isolated and characterized (Cadigan, et al. (1990) *J. Cell Biol.* 110:295–308; Gu, et al. (1997) *Proc. Natl. Acad. Sci. USA* 94:7378–83; Dahl, et al. (1992) *J. Biol. Chem.* 267:4889–96). Cholesterol trafficking activities of NPC1 mutants (CT43 and CT60) and their parental cell line 25RA have been shown (Chang and Limanek (1980) *J. Biol. Chem.* 255:7787–95; Hua, et al. (1996) *Cell* 87:415–26). NPC1 is involved in the transport of low-density lipoprotein (LDL)-derived cholesterol from internal compartments to the plasma membrane or to the ER (Cruz and Chang (2000) *J. Biol. Chem.* 275:41309–16; Pentchev, et al. (1985) *Proc. Natl. Acad. Sci. USA* 82:8247–51; Liscum, et al. (1989) *J. Cell Biol.* 108:1625–1636). NPC1 also participates in the transport of plasma membrane-derived cholesterol and endogenously synthesized cholesterol to the ER (Cruz and Chang (2000) supra; Cruz, et al. (2000) *J. Biol. Chem.* 275:4013–21; Pentchev, et al. (1985) supra; Byers, et al. (1992) *Biochim. Biophys. Acta* 1138:20–6; Lange, et al. (2000) *J. Biol. Chem.* 275:17468–75). Irrespective of the origin of cholesterol, the lack of a functional NPC1 protein invariably leads to cholesterol accumulation in the late endosome/lysosome.

Monitoring intracellular cholesterol transport using a biochemical approach is problematic as the isolation of distinct subcellular organelles in their pure states is difficult. Microscopic approaches have provided invaluable information. A well-known method for specifically detecting cholesterol in intact cells uses filipin, a naturally fluorescent polyene antibiotic that has high affinity towards cholesterol (Norman, et al. (1972) *J. Biol. Chem.* 247:1918–29), however, problems exist (Miller (1984) *Cell Biol. Int. Rep.* 8:519–35; Robinson and Karnovsky (1980) *J. Histochem. Cytochem.* 28:161–8; Severs and Simons (1983) *Nature* 303:637–8; Behnke, et al. (1984) *Eur. J. Cell Biol.* 35:200–15; Pelletier and Vitale (1994) *J. Histochem. Cytochem.* 42:1539–54). For example, the absorption spectrum of filipin is within the ultraviolet (UV) range and most of the commercially available confocal microscopes are not equipped with the laser beam that excites at the UV range; the fluorescence signal of filipin bleaches in a short time; in unfixed or fixed cells, filipin deforms the cellular membrane by forming complexes with cholesterol and causes perturbation of membrane lipid organization; and filipin has been reported to give false-negative results. Two fluorescent analogs of cholesterol, NBD-cholesterol and dehydroergosterol (DHE), have been used to track the fate of free sterol in the cell (Frolov, et al. (2000) *J. Biol. Chem.* 275:12769–80; Mukherjee, et al. (1998) *Biophys. J.* 75:1915–25). NBD-cholesterol exhibits a strong initial fluorescence signal at desirable wavelengths but bleaches quickly upon light exposure. Moreover, NBD-cholesterol does not consistently mimic the behavior of cholesterol inside the cells (Frolov, et al. (2000) supra). DHE behaves in a manner similar to cholesterol in many ways (Mukherjee, et al. (1998) supra). However, the fluorescence intensity of DHE is weak and it absorbs and emits in the UV region, therefore, special equipment is required in order to visualize DHE by fluorescence microscopy.

BCθ was developed as an effective tool for detecting cholesterol-rich domains (Waheed, et al. (2001) *Proc. Natl. Acad. Sci. USA* 98:4926–31; Iwamoto, et al. (1997) *Biochim. Biophys. Acta* 1327:222–30). BCθ is derived from a pore-forming cytolysin produced by the pathogenic bacterium *Clostridium perfringens* (Iwamoto, et al. (1997) supra). This thiol-activated cytolysin, called θ-toxin (or perfringolysin O), specifically binds to free (unesterified) cholesterol (Ohno-Iwashita, et al. (1990) *Biochim. Biophys. Acta* 1023:441–8; Ohno-Iwashita, et al. (1991) *J. Biochem.* (Tokyo) 110:369–75; Ohno-Iwashita, et al. (1992) *Biochim. Biophys. Acta* 1109:81–90; Nakamura, et al. (1995) *Biochemistry* 34:6513–20) and forms oligomeric pores in the membranes (Rossjohn, et al. (1997) *Cell* 89:685–92). BCθ is prepared by a two-step procedure. First, θ-toxin is proteolytically digested with subtilisin Carlsberg; this step generates a complex of 38- and 15-kDa fragments called Cθ (Ohno-Iwashita et al. (1986) *Biochemistry* 25:6048–53). Subsequently, the Cθ complex is biotinylated and purified, providing BCθ complex (Iwamoto, et al. (1997) supra). The biotinylation allows Cθ identification with avidin or streptavidin. When used in fluorescence microscopy, the labeling efficiency of BCθ depends on the qualities of fluorescent avidin and streptavidin. BCθ binds to cholesterol in synthetic liposomes and in intact cells with affinity identical to that of the wild-type θ-toxin, but because it does not oligomerize, it bears no hemolytic activity (Iwamoto, et al. (1997) supra; Ohno-Iwashita, et al. (1991) supra; Ohno-Iwashita, et al. (1992) supra). BCθ binds to cholesterol-rich microdomains in the plasma membrane of intact cells with or without fixation (Waheed, et al. (2001) supra; Hagiwara, et al. (1999) *Biochem. Biophys. Res. Commun.* 260:516–21; Mobius, et al. (2002) *J. Histochem. Cytochem.* 50:43–55); however, a means of detecting intracellular cholesterol using BCθ has not been demonstrated.

Accordingly, there is a need for a method of reliably and specifically detecting cholesterol for microscopic studies of intracellular cholesterol movement and accumulation.

SUMMARY OF THE INVENTION

One object of the present invention is to provide a method of detecting intracellular cholesterol using a labeled Cθ complex. The method provides contacting permeabilized cells with labeled Cθ complex and detecting binding of the Cθ complex to intracellular cholesterol.

Another object of the present invention is to provide a method of identifying agents which inhibit cholesterol accumulation using a high-throughput screening assay. In the assay of the present invention, mutant NCP1 cells, preferably CHO CT43 or CHO CT60 cells, are exposed to a test agent. The ability of the test agent to decrease levels of cholesterol accumulation in the cells is evaluated, preferably via labeled Cθ complex.

Methods of inhibiting over accumulation of cholesterol and treating or preventing diseases associated with over accumulation of cholesterol in cells are also provided.

These and other aspects of the present invention are set forth in more detail in the following description of the invention.

DETAILED DESCRIPTION OF THE INVENTION

Lipoproteins are macromolecular complexes that carry hydrophobic plasma lipids, particularly cholesterol and triglyceride in the plasma. More than half of the coronary heart disease in the United States is attributable to abnormalities in the levels and metabolism of plasma lipids and lipoproteins. Premature coronary heart disease is sometimes related to mutations in the major genes involved in lipoprotein metabolism. However, elevated lipoprotein levels in most patients with coronary heart disease reflect the adverse impact of excess body weight and diets high in total and saturated fats. Elevated lipoprotein levels in the brain have also been associated with neurodegenerative disorders such as Alzheimer's disease.

Treatment of elevated LDL cholesterol is typically focused at either disease prevention or secondary treatment after complications have occurred. The rationale for primary prevention is based on a large body of evidence linking elevated levels of LDL cholesterol with an increase in coronary heart disease as well as clinical and experimental data demonstrating that reducing LDL cholesterol slows progression and may actually induce regression of coronary heart disease.

Three classes of lipid-lowering agents are presently recommended as first line therapy against hypercholesteremia. These include bile acid sequestrants or binding resins, niacin and 3-hydroxy-3-methyl glutaryl-coenzyme A (HMG-CoA) inhibitors. However, there is a need for additional cholesterol inhibiting agents as well as screening assays to identify these agents.

The present invention provides a method for detecting intracellular cholesterol using labeled Cθ complex. The invention further provides a high-throughput screening assay using this detection method for use in evaluating and identifying test agents which modulate cholesterol accumulation.

It is well-known that biotinylated Cθ complex binds to plasma membrane-localized cholesterol, however, the present invention provides a method of detecting intracellular cholesterol by contacting permeabilized cells with labeled Cθ complex. By way of illustration only, intracellular cholesterol is detected in paraformaldehyde-permeabilized cells with biotinylated Cθ complex herein. 25RA and CT43 cells which were and were not permeabilized with a low concentration, i.e. 1.0%, of paraformaldehyde, were contacted with BCθ, subsequently labeled with fluorescent streptavidin, and viewed under a fluorescent microscope. Both concentrations of paraformaldehyde resulted in strong BCθ binding to cholesterol mainly in the vicinity of the cell surface. In addition, some intracellular binding was also observed. Unexpectedly, when either 25RA or CT43 cells were permeabilized with 4% paraformaldehyde at room temperature for more than 10 minutes, cell surface cholesterol binding by BCθ was significantly reduced; instead, BCθ mainly bound intracellular cholesterol-rich domains. This indicated that 4% paraformaldehyde permeabilizes the cell, making BCθ accessible to the intracellular region. Control experiments provided no detectable fluorescence signal in cells contacted with fluorescent streptavidin alone without BCθ. Reduced cell surface binding of cholesterol by BCθ in cells permeabilized with 4% paraformaldehyde may be the consequence of severe deformation/reorganization of the plasma membrane which in turn inhibits the binding of BCθ to cholesterol at the plasma membrane. A similar reduction in BCθ binding to cell surface cholesterol of cells pre-fixed with 2% formaldehyde has been observed by electron microscopy and flow cytometry (Mobius, et al. (2002) supra).

Flow cytometric analysis of CHO cells grown in lipoprotein-containing medium was performed to quantitate fluorescent signal produced by BCθ binding. As a negative control, 25RA cells contacted with fluorescent streptavidin alone without BCθ were used. Wild-type CHO and mutant M19 cells were included in some experiments as additional controls. Plasma membrane and intracellular cholesterol content is provided in Table 1.

TABLE 1

| Cell Line | Treatment | Mean Fluorescence Intensity | % Cells in M1 Range* |
|---|---|---|---|
| 25RA | Live Cell | 791.6 | 94.6 |
| CT43 | Detection | 829.0 | 95.6 |
| Wild-Type | | 651.6 | 64.0 |
| M19 | | 490.0 | 14.8 |
| 25RA | Permeabilized with | 485.0 | 5.5 |
| CT43 | 1% Paraformaldehyde | 519.8 | 11.6 |
| 25RA | Permeabilized with | 611.9 | 34.4 |
| CT43 | 4% Paraformaldehyde | 707.2 | 82.4 |

*M1 is defined as the region of fluorescence intensity that contains less than 0.1% of control cells (no BCθ incubation, with streptavidin only) for each detection method.

The 25RA and CT43 cells contain a gain of function mutation in the SREBP cleavage activating protein (SCAP) (Hua, et al. (1996) *Cell* 87:415–26). As a result, these cells constitutively express the LDL receptor and various cholesterol biosynthetic enzymes at elevated levels. In contrast, the M19 cells lack the S2P gene that is essential for activating the SREBP pathway (Chin and Chang (1981) *J. Biol. Chem.* 256:6304–6310; Rawson, et al. (1997) *Mol. Cell* 1:47–57). M19 cells express the LDLR and various cholesterol biosynthetic enzymes at levels lower than those in the wild-type cells.

Live cell detection demonstrated that both 25RA and CT43 cells exhibited stronger fluorescence intensities than the wild-type cells, while the M19 cells exhibited weaker fluorescence intensities than the wild-type cells. Furthermore, 25RA and CT43 cells had a greater percentage of cells with a strong positive signal than the wild-type cells, while the M19 cells had a much lower percentage of cells exhibiting a strong positive signal than the wild-type cells. It was also noted that the average fluorescence signal was slightly higher in CT43 cells than in 25RA cells. These results indicate that the bulk plasma membrane cholesterol content may not be significantly altered in the CT43 cells.

Additional flow cytometric analysis of cells contacted with BCθ was conducted using 25RA cells and CT43 cells permeabilized with 1% or 4% paraformaldehyde. Upon 1% paraformaldehyde permeabilization, where plasma membrane cholesterol detection is predominant, CT43 cells showed slightly higher levels of BCθ binding than 25RA cells. When cells were permeabilized with 4% paraformaldehyde prior to BCθ binding, a higher fluorescence intensity and higher percentage of strong positive cells was observed in both cell types. Moreover, BCθ binding was much higher in CT43 cells than in the 25RA cells, indicating that most of the fluorescent signal comes from cholesterol accumulated intracellularly. These results demonstrate that permeabilizing cells with 4% paraformaldehyde facilitates accessibility of BCθ to intracellular cholesterol of CHO cells, without the need for any additional permeabilization procedure.

A comparison of cholesterol detection using filipin or BCθ was conducted. 25RA and CT43 cells were grown in medium A containing FBS or in medium D containing delipidated FBS and parallel filipin and BCθ analyses were performed. Binding was detected using fluorescence microscopy. When cells were grown in medium A, BCθ was able to bind to intracellular cholesterol in both 25RA and CT43 cells, with CT43 cells providing considerably more signal. In contrast, filipin was able to bind intracellular cholesterol in CT43 cells but not in 25RA cells. When cells were grown for 16 hours in medium containing delipidated FBS (medium D), intracellular cholesterol content was reduced in both 25RA and CT43 cells, as determined by BCθ binding. Under the same conditions, filipin detected the decrease in intracellular cholesterol content in CT43 cells, but not in 25RA cells. In addition, sequential binding of BCθ followed by filipin completely abolished filipin signal in NPC1 cells, indicating that filipin may be binding to the same intracellular cholesterol-rich domains as BCθ. These results demonstrate that BCθ is superior to filipin for detecting cholesterol-rich domains in intracellular organelles.

To examine the effect of NPC1 expression on intracellular BCθ binding to cholesterol in CT43 cells, a construct comprising a GFP-tagged NPC1 protein (NPC1-GFP) was prepared and introduced into CT43 cells by transient transfection. NPC1-GFP has been used to detect the trafficking and function of the NPC1 protein in transfected cells (Ko, et al. (2001) *Mol. Biol. Cell* 12:601–14; Zhang, et al. (2001) *Proc. Natl. Acad. Sci. USA* 98:4466–71). After BCθ binding, cells containing NPC1-GFP were viewed in the red channel to detect the BCθ fluorescence signal or in the green channel to detect the NPC1-GFP fluorescence signal. The two fluorescence signals were then merged to examine their degree of overlap. Cells expressing NPC1-GFP exhibited significantly reduced BCθ fluorescence signal compared to cells that did not express the fusion protein; no fluorescence overlap was observed between the red and green channels. As a control, CT43 cells expressing only GFP did not show reduced BCθ fluorescence signal. U18666A is a polyamine-containing compound that induces an NPC1-like phenotype when added to cells expressing wild-type NPC1 (Lange, et al. (2000) *J. Biol. Chem.* 275:17468–75; Liscum and Faust (1989) *J. Biol. Chem.* 264:11796–806). When CT43 cells expressing NPC1-GFP were exposed to U18666A, binding of BCθ to intracellular cholesterol persisted. Moreover, binding of BCθ significantly overlapped with the GFP signal. Thus, the intracellular cholesterol-rich domain visualized by binding of BCθ significantly co-localized with the compartment(s) that contains NPC1-GFP in cells exposed to U18666A. Similar observations have been made using filipin to detect intracellular cholesterol (Watari, et al. (2000) *Exp. Cell Res.* 255:56–66). These results further demonstrate that the cholesterol-rich compartment(s) detected by BCθ in NPC1 cells may be the same compartment(s) identified by filipin.

The effect of cyclodextrin on binding of BCθ to intracellular cholesterol of 25RA and CT43 cells was examined. β-cyclodextrin is a cyclic oligosaccharide that specifically and rapidly removes free cholesterol from the cell membranes when added to growth media (Rothblat, et al. (1999) *J. Lipid Res.* 40:781–96). Changes in the intracellular distribution of cholesterol in 25RA and CT43 cells exposed to 2-hydroxypropyl-b-cyclodextrin (hpCD) was detected using BCθ. Upon exposing cells to 4% hpCD for 10 minutes, both cell lines retained most of the BCθ fluorescence signals, indicating that only cholesterol at the cell surface is easily accessible to cyclodextrin. When the hpCD exposure was extended to 60 minutes, 25RA cells emitted much less BCθ fluorescence signal, whereas CT43 cells retained much of the signal. These results indicate that the intracellular cholesterol pool in 25RA cells is sensitive to cyclodextrin extraction, while most of the intracellular cholesterol pool in CT43 cells is relatively resistant to cyclodextrin extraction.

Binding of BCθ to intracellular cholesterol in other cell types, such as human and mouse fibroblasts, was evaluated. Both wild-type and NPC1 human fibroblasts grown in medium A exhibited binding of BCθ to intracellular cholesterol, with much greater fluorescence signals present in the NPC1 cells. When cells were grown for 36 hours in medium D, wild-type cells lost most of the BCθ fluorescence signal, while the NPC1 cells retained much of the fluorescence signal. When cells were grown 120 hours in medium D, BCθ binding was not detected in either cell type. Binding of BCθ to intracellular cholesterol of embryonic fibroblasts isolated from wild-type, NPC+/−, or NPC−/− mice was examined. Fibroblasts grown in medium A showed intensities of intracellular fluorescence attributable to BCθ binding in the order of NPC1−/−>NPC1+/−>NPC1+/+. After maintaining cells in medium D for 48 hours, neither NPC1+/+ nor NPC1+/− cells had a detectable BCθ fluorescence signal. In contrast, the NPC1−/− fibroblasts retained much of the BCθ fluorescence signal.

Accordingly, a first aspect of the invention provides a method of detecting intracellular cholesterol in permeabilized cells using labeled Cθ complex. The method comprises contacting cells with a reagent which not only fixes but also physically or chemically permeabilizes the cell membrane to facilitate up-take and binding of labeled Cθ complex to intracellular cholesterol. Permeabilization typically occurs at a temperature ranging from approximately 4° C. to 37° C. C for a period of time from approximately 10 minutes to 60 minutes. As provided herein, paraformaldehyde was used to permeabilize cells at a concentration ranging from 3% to 4%, however, as one of skill in the art will appreciate, other reagents including, but not limited to, chilled methanol (100%), TRITON™ X-100 (e.g., 0.1%–1.%), digitonin (e.g., 30 μg/ml–40 μg/ml), and saponin (e.g., 0.05%–0.25%) may also be used to permeabilize cells after mild fixation with 1.0% or lower concentration of paraformaldehyde. In a preferred embodiment the cells are fixed and permeabilized with 4% paraformaldehyde prior to the addition of labeled Cθ complex. The extent of permeabilization of a cell by a permeabilizing reagent may vary and is dependent on factors such as cell type, culture medium, and temperature. A cell is said to be permeabilized if labeled Cθ complex is taken up by the cell in an amount sufficient to bind and detect intracellular cholesterol. Permeabilization may also be determined using other well-known methods such as phalloidin uptake.

After permeabilization, cells are contacted with labeled Cθ complex. Suitable labeled Cθ complexes include Cθ complex directly conjugated to biotin or a fluorescent label used for cell analysis. Fluorescent labels may be attached directly to the Cθ complex through sulfhydryl or primary amine groups.

Exemplary fluorescent labels include, but are not limited to, (α-Phycoerythrin, Green Fluorescent Protein, Phycocyanine, Allophycocyanine, Tricolor, AMCA, AMCA-S, AMCA, BODIPY FL, BODIPY 493/503, BODIPY FL Br2, BODIPY R6G, BODIPY 530/550, BODIPY TMR, BODIPY 558/568, BODIPY 564/570, BODIPY 576/589, BODIPY 581/591, BODIPY TR, Cascade Blue, CI-NERF, Dansyl, Dialkylaminocoumarin, 4',6'-Dichloro-2', 7'-dimethoxyfluorescein, 2',7'-dichloro-fluorescein, Cy3, Cy5, Cy7, DM-NERF, Eosin, Eosin F3S, Erythrosin, Fluorescein, Fluorescein Isothiocyanate Hydroxycoumarin, Isosulfan Blue, Lissamine Rhodamine B, Malachite Green, Methoxycoumarin, Napthofluorecein, NBD, Oregon Green 488, Oregon Green 500, Oregon Green 514, Propidium Iodide Phycoerythrin, PyMPO, Pyrene, Rhodamine 6G, Rhodamine Green, Rhodamine Red, Rhodol Green, 2',4',5',7'-Tetrabromosulfonefluorescein, Tetramethyl-rhodamine, Texas Red, X-rhodamine; Lucifer Yellow, and the like.

The time required for binding labeled Cθ complex may vary with temperature, extent of permeabilization and cell type and is in the range of 10 to 30 minutes. Additional reagents may be added to the medium containing the labeled Cθ complex to decrease non-specific binding interactions or improve the stability of the labeled Cθ complex, e.g., bovine serum albumin or other reagents known to have such properties. Subsequently, the cells may be washed to remove any residual or non-specifically bound labeled Cθ complex prior to imaging and analysis.

Detection of labeled Cθ complex bound to cholesterol will be dependent on the label which is conjugated to the Cθ complex. For example, detection of biotinylated Cθ may be performed using any of the well-known avidin or streptavidin reagents. Detection of biotin-avidin or biotin-streptavidin complexes typically involves conjugated forms of avidin or streptavidin including, but are not limited to, enzyme-conjugates (e.g., alkaline phosphatase, β-galactosidase, glucose oxidase, horseradish peroxidase) or fluorescent-conjugates (e.g., 7-amino-4-methylcoumarin-3-acetic (AMCA), fluorescein, phycoerythrin, rhodamine, TEXAS RED®, OREGON GREEN®) or antibodies which specifically bind to avidin or streptavidin. Methods of detecting antibodies are well-known to those of skill in the art (see, e.g., "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984) *J. Clin. Chem. Clin. Biochem.* 22:895–904) It is preferred that the label to be imaged is fluorescent, i.e. either a Cθ complex conjugated to fluorescent label or avidin or streptavidin conjugated to fluorescent label.

Methods of imaging and analyzing any of the above-mentioned labels are well-known in the art and the method employed will vary with the type of analysis being conducted, i.e. individual samples or multiple sample analyses in high-throughput screens. Preferably, measurement of the label is accomplished using flow cytometry, laser confocal microscopy, spectrofluorometer, fluorescence microscopy, fluorescence scanners and the like.

The detection method of the invention has broad applicability and may be used for the detection of cholesterol in mammalian and non-mammalian eukaryotic cells including, for example, plant cells.

A second aspect of the present invention provides a method of identifying agents which modulate cholesterol accumulation. The method of the invention is a cell-based assay which uses cells with a defective or mutant NCP1 gene. As one of skill in the art will appreciate, mammalian or non-mammalian cell may be used in the assay of the invention to identify agents which modulate cholesterol accumulation. It is preferred that the mutant NCP1 cells comprise CHO CT43 or CT60 cells. CHO CT43 cells have been described and characterized in detail (see, e.g., Cruz, et al. (2000) supra; Cruz and Chang (2000) supra) as have CHO CT60 cells (see, e.g., Cadigan, et al. (1990) supra). In the screening assay of the present invention, the mutant NCP1 cells are exposed to a test agent. The ability of the test agent to modulate cholesterol accumulation in the cells, as determined by binding and detection of BCθ or a derivative thereof, is then evaluated. Levels of cholesterol accumulation in mutant cells exposed to the test agent are compared to levels of cholesterol accumulation in mutant cells not exposed to the test agent. A decrease in cholesterol accumulation in these mutant cells is indicative of the test agent being a cholesterol inhibitor. In a preferred embodiment of the present invention, the mutant cells comprise CHO CT43 or CT60 cells and levels of cholesterol accumulation in these cells when exposed to a test agent are compared to levels of cholesterol accumulation in parental 25RA cells not exposed to the test agent. In this embodiment, test agents which decrease the level of cholesterol accumulation in the mutant cells to a level similar to the level in parental 25RA cells are expected to be potent cholesterol inhibitors.

It is preferred that the screening assay of the present invention be performed in a microtiter well format so that multiple test agents at various concentrations can be evaluated simultaneously. In this embodiment, mutant NPC1 cells are seeded into the wells of a microtiter plate. Cholesterol accumulation is preferably measured via the BCθ detection method provided herein. In addition to mutant NCP1 cells exposed to various test agents, it is preferred that additional wells containing only mutant cells and only parental cells also be included as negative and positive controls, respectively, for the assay. Wells containing only mutant cells provide a negative control wherein cholesterol accumulation is expected to be high. These negative controls can be used to compare and determine decreases in levels of cholesterol accumulation of the mutant cells upon exposure to the test agents. Decreases in levels of cholesterol accumulation in cells upon exposure to the test agent as compared to the negative control are indicative of the test agent being a cholesterol inhibitor. Wells containing the parental cells provide a positive control of levels of cholesterol accumulation in normal cells. Test agents which decrease levels of cholesterol accumulation to levels similar to that of the positive control are expected to be very effective cholesterol inhibitors.

In a preferred embodiment, the mutant cells used in the microtiter well format comprise CT43 cells or CT60 cells and are seeded at approximately $3-4 \times 10^4$ cells per well in medium A comprising Ham's F-12, 10% FBS, and 10 μg/ml gentamycin. Control cells comprising the parental 25RA cells are seeded at approximately $1 \times 10^4$ cells/well. The medium is removed after one day and various test agents and/or various concentrations of a single test agent are then added to the wells and the plates are grown for about 14 hours before intracellular detection using BCθ.

In another preferred embodiment, the cells receive a pulse of LDL cholesterol prior to exposing the cells to the test agent. In this embodiment, the mutant cells (CT43 or CT60) are seeded at approximately $3-4 \times 10^4$ cells per well in medium A comprising Ham's F-12, 10% FBS, and 10 μg/ml gentamycin. Control cells comprising the parental 25RA cells are seeded at approximately $1 \times 10^4$ cells/well. In this embodiment, the medium is removed after one day, the cells are rinsed with phosphate buffered saline (PBS) and the medium is changed to Medium D comprising Ham's F12, 5% delipidated FBS, 35 μM oleic acid, and 10 μg/ml gentamycin. The CT43 or CT60 cells are then grown for an additional 36 hours. Cells are then washed and various test agents and/or various concentrations of a single test agent are then added to the wells and the plates are incubated at approximately 37° C. for about one hour. Subsequently, the cells are grown in the presence of LDL cholesterol (approximately 100 μg LDL/ml medium in 0.1 ml of medium D) at approximately 37° C. for about 14 hours.

In a preferred embodiment, the test agents are dissolved at high concentration in a solvent such as dimethyl sulfoxide (DMSO) so that the final concentration of the solvent in the assay is less than or equal to 1%. Typical concentrations of test agents range from 1 to 100 μM. Following exposure to the test agent, cholesterol accumulation is evaluated using the labeled Cθ complex detection method provided herein.

Agents identified as cholesterol inhibitors in accordance with the method of the present invention can block the internalization of LDL-derived cholesterol and/or plasma membrane cholesterol from entering the cell interior thereby causing cholesterol to accumulate in the plasma membrane and promoting cholesterol efflux and stimulating reverse cholesterol transport in various body cells. These agents are expected to slow the development of atherosclerosis. Agents identified as inhibitors in accordance with the method of the present invention can also block the internalization of plasma membrane cholesterol in intestinal enterocytes, thereby preventing dietary cholesterol absorption. Such agents can also slow down the accumulation of amyloid beta-peptides in the brain, thereby slowing down the symptoms of Alzheimer's disease. Accordingly, test agents identified as cholesterol inhibitors in accordance with the assay of the present invention are expected to be useful in preventing and treating cardiovascular and neurodegenerative disease associated with over accumulation of cholesterol in cells. Such agents are also expected to be useful in the treatment of Niemann Pick type C disease.

The invention is described in greater detail by the following non-limiting examples.

EXAMPLE 1

Materials

LDL was prepared from fresh human plasma by sequential flotation using well-known methods (Cadigan, et al. (1988) *J. Biol. Chem.* 263:274–282). BCθ was prepared according to standard methods (Waheed, et al. (2001) supra). Briefly, θ-toxin was overexpressed in *Escherichia coli* strains, purified by a series of chromatography steps (Shimada, et al. (1999) *J. Biol. Chem.* 274:18536–42), and digested with subtilisin Carlsberg to produce a nicked θ-toxin (Cθ) (Ohno-Iwashita et al. (1986) supra). BCθ was then obtained by biotinylating Cθ using well-known methods (Iwamoto, et al. (1997) supra).

EXAMPLE 2

Cell Lines

25RA is a CHO cell line resistant to the cytotoxicity of 25-hydroxycholesterol (Chang and Limanek (1980) supra) and contains a gain of function mutation in the SCAP (Hua, et al. (1996) *Cell* 87:415–26). CT60 and CT43 mutant are isolated as two of the cholesterol trafficking mutants from mutagenized 25RA cells (Cadigan, et al. (1990) supra). Both mutants contain premature translational termination mutations in the NPC1 coding sequence, producing a non-functional, truncated NPC1 protein (Cruz, et al. (2000) supra).

EXAMPLE 3

Cell Culture

CHO cells were maintained in medium A (Ham's F-12, plus 10% fetal bovine serum (FBS) and 10 µg/ml gentamycin) as monolayers at 37° C. with 5% $CO_2$. Medium D refers to Ham's F-12 with 5% delipidated FBS (Chin and Chang (1981) *J. Biol. Chem.* 256:6304–6310), plus 35 µM oleic acid, and 10 µg/ml gentamycin. When medium D was used at lower temperatures (below 18° C.), sodium bicarbonate was depleted from Ham's F-12 and cells were placed in the incubator without $CO_2$.

2-hydroxypropyl-β-cyclodextrin (SIGMA™-Aldrich, St. Louis, Mo.) was added to culture medium using well-known methods (Rothblat, et al. (1999) supra). U18666A was provided to the cells using standard conditions (Lange, et al. (2000) supra; Liscum and Faust (1989) supra).

EXAMPLE 4

Construction and Transfection of GFP-Tagged NPC1

A polymerase chain reaction (PCR) fragment was generated using a GFP CDNA as the template and a 5' primer whose sequence corresponds to the mouse NPC1 C-terminal sequence from the Eco47III site to the end of open reading frame (ORF) (except the stop codon), followed by a 6×-Ala spacer sequence, which is in turn followed by a sequence corresponding to the N-terminal sequence of GFP. The 3' primer consists of sequences corresponding to the C-terminal sequence of GFP and to HindIII and XhoII restriction sites. The resulting PCR product was digested with HindIII and Eco47III and ligated into an NPC1-containing pBLUE-SCRIPT® plasmid (STRATAGENE®, La Jolla, Calif.) that had been digested with HindIII and Eco47III and gel purified. A SpeI-HindIII fragment of NPC1-GFP was further subcloned into the pREX-IRES vector (Liu, et al. (2000) *Anal. Biochem.* 280:20–8). Transient transfection of NPC1-GFP was performed in CT43 cells using FUGENE™ 6 according to manufacturer's instructions (Roche, Indianapolis, Ind.). Transfected cells were imaged within 2–3 days of transfection.

EXAMPLE 5

Fluorescence Microscopy

Cells were grown on glass coverslips in six-well plates and processed for fluorescence studies. The effect of residual serum adhering to the coverslips was minimized by incubating cells in a serum-free medium for two hours before the experiments, however, it was noted that no difference in results was obtained with or without the preincubation step. For BCθ binding in premeabilized cells, the cells were washed three times, and permeabilized with 4% or 1% paraformaldehyde (SIGMA™-Aldrich, St. Louis, Mo. and Electron Microscopy Sciences, Ft. Washington, Pa.; similar results obtained from each supplier) in phosphate-buffered saline (PBS) for 10 minutes or longer at room temperature. After extensive washes with PBS, the cells were pre-incubated in PBS containing 1% bovine serum albumin (BSA), then 10 µg/ml BCθ in 1% BSA-PBS was added and the cells were incubated for 30 minutes at room temperature. After washing three times, the cells were exposed to either OREGON GREEN® 488-conjugate streptavidin (1 µg/ml; Molecular Probes, Eugene, Oreg.) or TEXAS RED® X-conjugated streptavidin (1 µg/ml; Molecular Probes, Eugene, Oreg.) in PBS with 1% BSA at room temperature. After three washes, the coverslips were mounted with a drop of PROLONG® Anti-Fade media (Molecular Probes, Eugene, Oreg.) onto the glass plates for image processing. The protocol for detecting cholesterol using filipin was essentially the same except that cells were pre-incubated with 1.5 mg/ml glycine in PBS for 30 minutes, then incubated with filipin (125 µg/ml; SIGMA™-Aldrich, St. Louis, Mo.) in PBS for one hour at room temperature before image processing. For live cell detection, cells were chilled and kept on ice, washed three times, pre-incubated in ice-cold phenol red-free Hank's balanced salt solution (HBSS) containing 1% BSA, then contacted with 10 μg/ml BCθ in the same solution for 30 minutes at 4° C. After washing three times with HBSS, the cells were incubated with fluorescent streptavidin in HBSS with 1% BSA at 4° C., and processed for image analysis. Samples were viewed and photographed using a ZEISS® Axiophot microscope with a 63× objective equipped with CCD camera DEI-750 (Optronics Engineering, Goleta, Calif.). DAPI filter, FITC filter, and TEXAS RED® filter were used to visualize filipin, GFP/OREGON GREEN® 488, and TEXAS RED® X, respectively. The image was processed by using the METAVIEW™ 4.5 software (UNIVERSAL IMAGING CORPORATION™, Downingtown, Pa.). To confirm the validity of some co-localization studies, the samples were also observed with a MRC-1024 Krypton/Argon laser confocal microscope (BIO-RAD®, Hercules, Calif.).

EXAMPLE 6

Flow Cytometry

Cells were processed for cholesterol detection with BCθ with OREGON GREEN® 488-streptavidin essentially as described above except that the cells (~1×10$^6$) were suspended in 1.5 ml size microtubes with careful mixing and pelleted by brief centrifuge after each washing step. Subsequently, the cells were resuspended in 1 ml of 1% BSA in either HBSS (for live cell detection) or PBS (for permeabilized cell detection). The cells were analyzed at an excitation wavelength of 488 nm and emission wavelength of 515–530 nm, using a FACSCAN™ cytometer with CELLQUEST™ software (Becton Dickinson, San Jose, Calif.).

What is claimed is:

1. A method for identifying an agent that modulates intracellular cholesterol accumulation comprising exposing mutant NPC1 cells to a test agent, permeabilizing the mutant NPC2 cells, evaluating the intracellular level of cholesterol accumulation in the permeabilized mutant NPC1 cells exposed to the test agent via binding of labeled Cθ complex to cholesterol-rich domains in intracellular organelles, and comparing the evaluated level to the intracellular level of cholesterol bound to labeled Cθ complex in mutant NPC1 cells not exposed to the test agent, wherein a decrease in the intracellular level of cholesterol accumulation in the mutant NPC1 cells exposed to the test agent as compared to the intracellular level in mutant NPC1 cells not exposed to the test agent is indicative of the test agent being a cholesterol inhibitor.

2. The method of claim 1 wherein the mutant NPC1 cells comprise CHO CT43 or CT60 cells.

3. A method for identifying an agent that modulates intracellular cholesterol accumulation comprising exposing mutant NPC2 cells to a test agent, permeabilizing the mutant NPC1 cells, evaluating the intracellular level of cholesterol accumulation in the mutant NPC1 cells exposed to the test agent via binding of labeled Cθ complex to cholesterol-rich domains in intracellular organelles, and comparing the evaluated level to the intracellular level of cholesterol bound to labeled Cθ complex in parental cells not exposed to the test agent, wherein the intracellular level of cholesterol accumulation in the mutant NPC1 cells exposed to the test agent is equal to the intracellular level of cholesterol in the parental cells not exposed to the test agent is indicative of the test agent being a cholesterol inhibitor.

4. The method of claim 3 wherein the mutant NPC1 cells comprise CHO CT43 or CT60 cells and the parental cells comprise CHO 25RA cells.

* * * * *